(12) United States Patent
Guala

(10) Patent No.: US 8,486,049 B2
(45) Date of Patent: Jul. 16, 2013

(54) VALVE CONNECTOR FOR MEDICAL LINES

(75) Inventor: Gianni Guala, Turin (IT)

(73) Assignee: Industrie Borla S.p.A., Moncalieri (Torino) (IT)

( * ) Notice: Subject to any disclaimer, the term of this patent is extended or adjusted under 35 U.S.C. 154(b) by 360 days.

(21) Appl. No.: 12/686,163

(22) Filed: Jan. 12, 2010

(65) Prior Publication Data
US 2010/0179514 A1    Jul. 15, 2010

(30) Foreign Application Priority Data
Jan. 14, 2009    (IT) .............................. TO2009A0024

(51) Int. Cl.
*A61M 39/00* (2006.01)
(52) U.S. Cl.
USPC .......................................... 604/533; 604/284
(58) Field of Classification Search
USPC ........................... 604/533, 68, 536–539, 284
See application file for complete search history.

(56) References Cited

U.S. PATENT DOCUMENTS

2006/0111694 A1* 5/2006 Fukai et al. .................... 604/905
2007/0218757 A1* 9/2007 Guala ........................... 439/589

FOREIGN PATENT DOCUMENTS

| EP | 1 584 346 | 10/2005 |
| EP | 1 834 665 | 9/2007 |

OTHER PUBLICATIONS

Italian Search Report for Italian Patent Application No. TO2009A000024, dated Oct. 20, 2009.
Italian Written Opinion for Italian Patent Application No. TO2009A000024, 4 pages.

* cited by examiner

*Primary Examiner* — Kevin C Sirmons
*Assistant Examiner* — Deanna K Hall
(74) *Attorney, Agent, or Firm* — Nixon & Vanderhye P.C.

(57) ABSTRACT

A valve connector for medical infusion lines including a tubular body (1) with an inlet (4) and an outlet (10), an internal hollow spike (2), and a sealing member (3) including an elastic head (14) with pre-slit (17) normally kept in an undeformed closed condition within the inlet (4). The outlet (10) comprises a pierceable injection point (22) coaxially facing the hollow spike (2).

1 Claim, 9 Drawing Sheets

VALVE CONNECTOR FOR MEDICAL LINES

BACKGROUND OF THE INVENTION

The present invention relates to valve connectors for medical lines, for example, infusion lines, which can be coupled to a fluid introducer, for example, in the form of a Luer or Luer-Lok connector.

STATE OF THE PRIOR ART

More in particular, the invention regards a valve connector of the type described and illustrated in the European patent application No. EP-1834665A1 filed in the name of the present applicant. Said valve connector comprises a tubular body having an inlet for engagement of the fluid introducer and an outlet, and a hollow spike set axially within the cavity of the tubular body and having a closed tip facing the inlet and set at an axial distance from the latter. The hollow spike is in communication with the outlet of the tubular body, and the connector moreover includes a sealing member comprising an elastic head with pre-slit, which is normally set in an undeformed condition within the inlet of the tubular body, in which the pre-slit is closed, and can be displaced axially against the closed terminal of the hollow spike, as a result of insertion of the fluid introducer within the inlet, to assume an elastically deformed condition of opening of the pre-slit. The sealing member moreover includes a hollow elastic element joined to the elastic head and defining an elastic thrust means that tends to keep the head in the aforesaid undeformed condition.

In the valve connector according to the aforesaid document No. EP-1834665A1 the outlet consists of a male Luer-Lok connection member (possibly also of some other type) conveniently formed in a single piece with the hollow spike and set coaxially with respect to the inlet.

SUMMARY OF THE INVENTION

The present invention constitutes an improvement of the invention disclosed in the aforesaid document No. EP-1834665A1 and, more in particular, has the purpose of extending the sphere of use of the valve connector as defined above.

According to the invention, said object is achieved thanks to the fact that the outlet of the tubular body comprises a pierceable injection point, coaxially facing the aforesaid hollow spike.

In the description and in the ensuing claims, the term "pierceable" is used to refer both to an element that can be traversed by the needle of a syringe or the like and to a pre-slit element that can be traversed by the cannula of a needleless syringe or the like.

According to the invention, the aforesaid pierceable injection point consists of a diaphragm made of elastic material blocked within a terminal tubular appendage of the hollow spike.

In addition to the point that can be pierced by a needle, the outlet of the valve connector according to the invention moreover advantageously includes at least one lateral tubular fitting set transverse to the aforesaid terminal tubular appendage. Preferably, a pair of opposed lateral tubular fittings is provided, formed integrally with the hollow spike, together with the aforesaid terminal lateral appendage.

BRIEF DESCRIPTION OF THE DRAWINGS

The invention will now be described in detail with reference to the annexed drawings, which are provided purely by way of non-limiting example and in which.

DETAILED DESCRIPTION OF THE INVENTION

Figure 1:
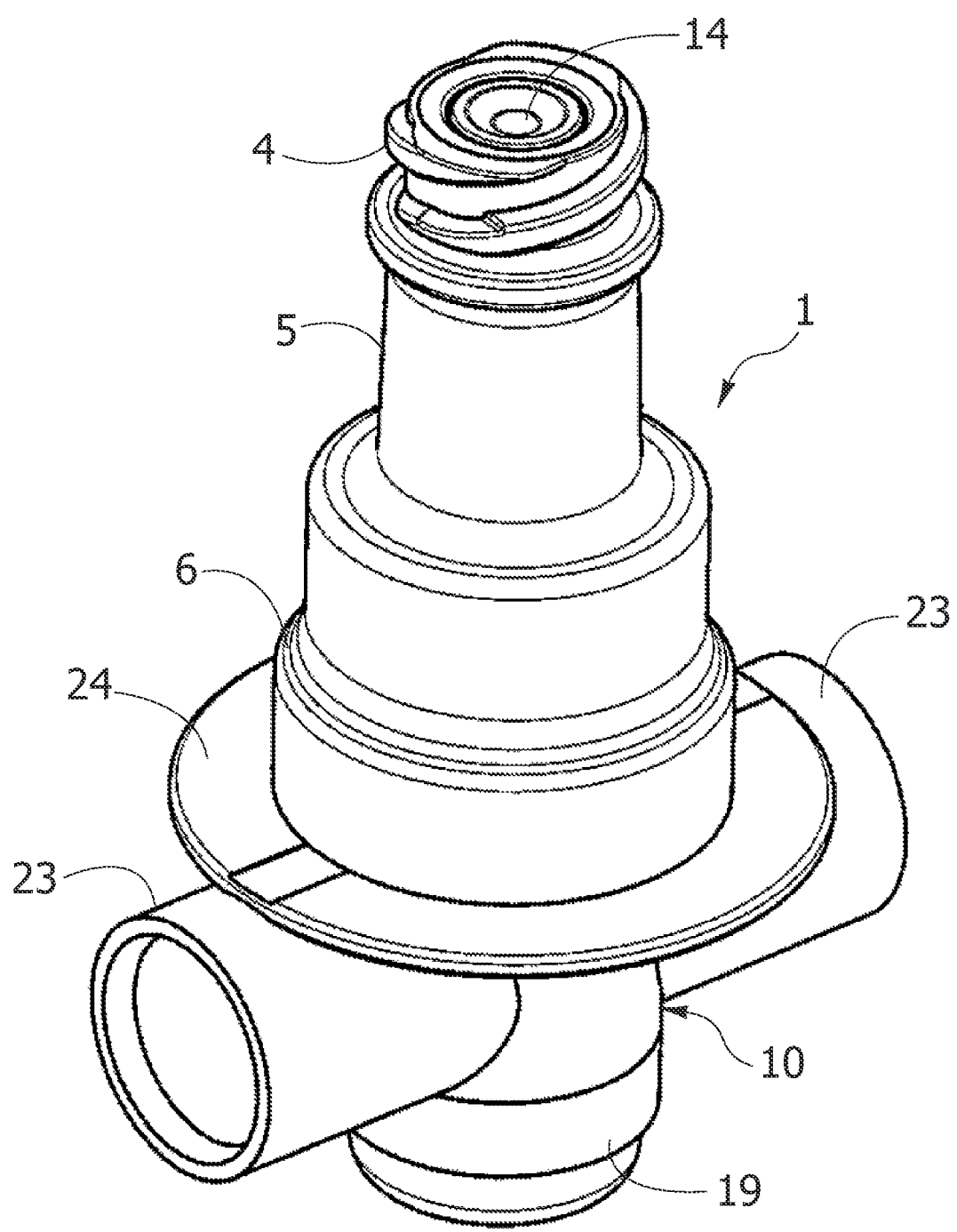
FIG. 1 is a schematic perspective view of a valve connector according to one embodiment of the invention.
Figure 2:
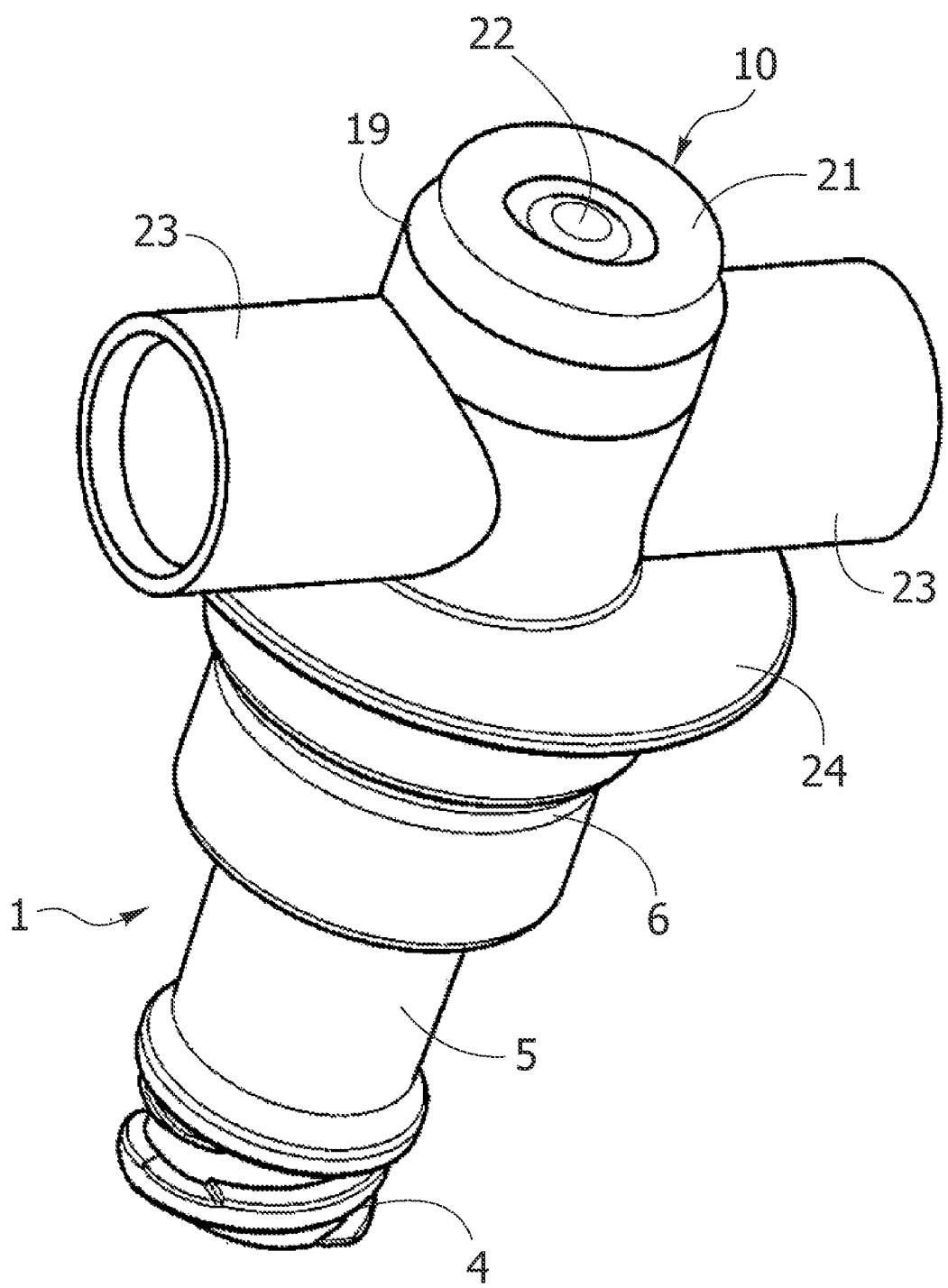
FIG. 2 is a view from beneath of the valve connector of FIG. 1.
Figure 3:
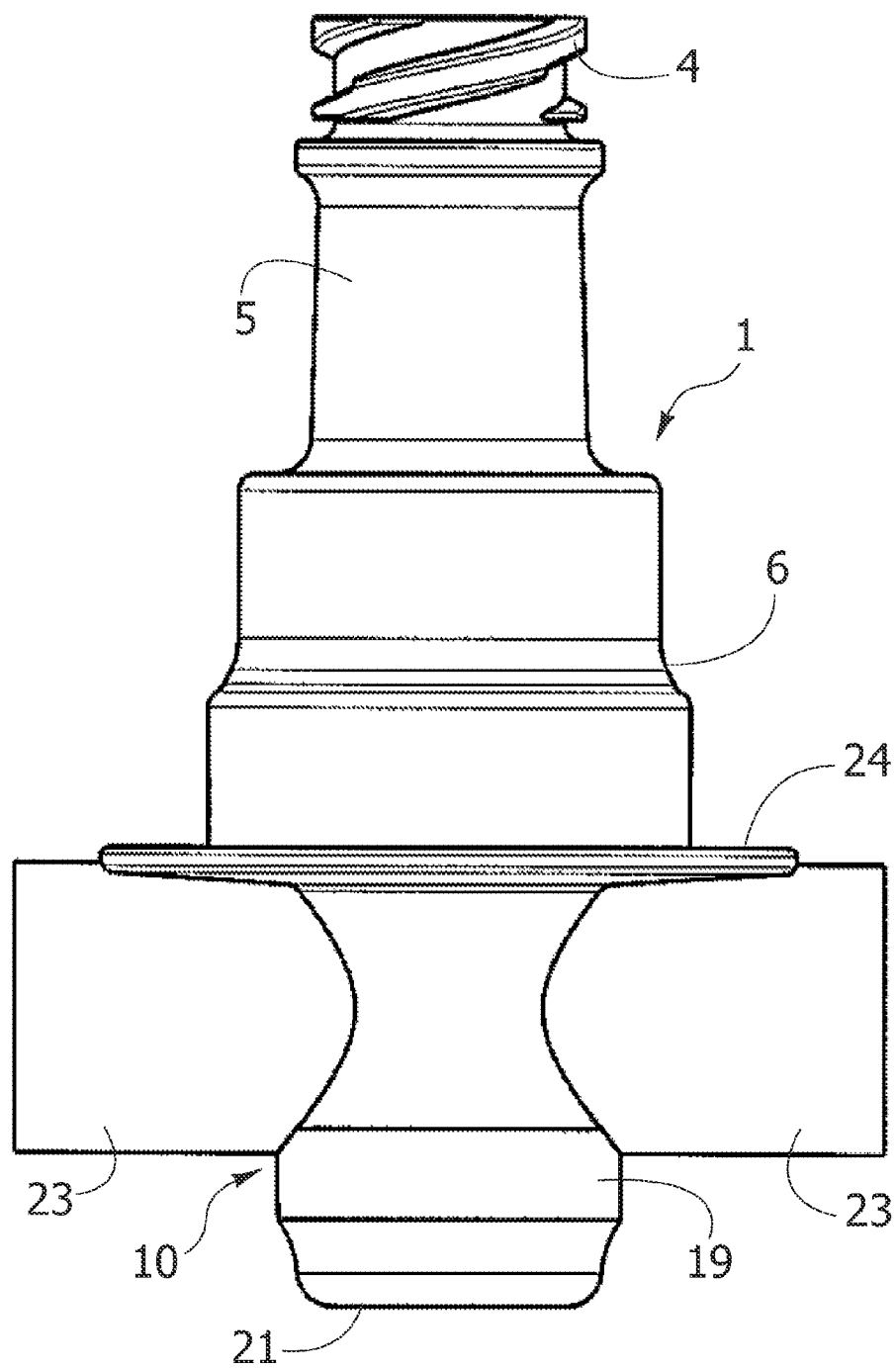
FIGS. 3 and 4 are two views in side elevation of the valve connector according to FIG. 1, rotated with respect to one another by 90°.
Figure 4:
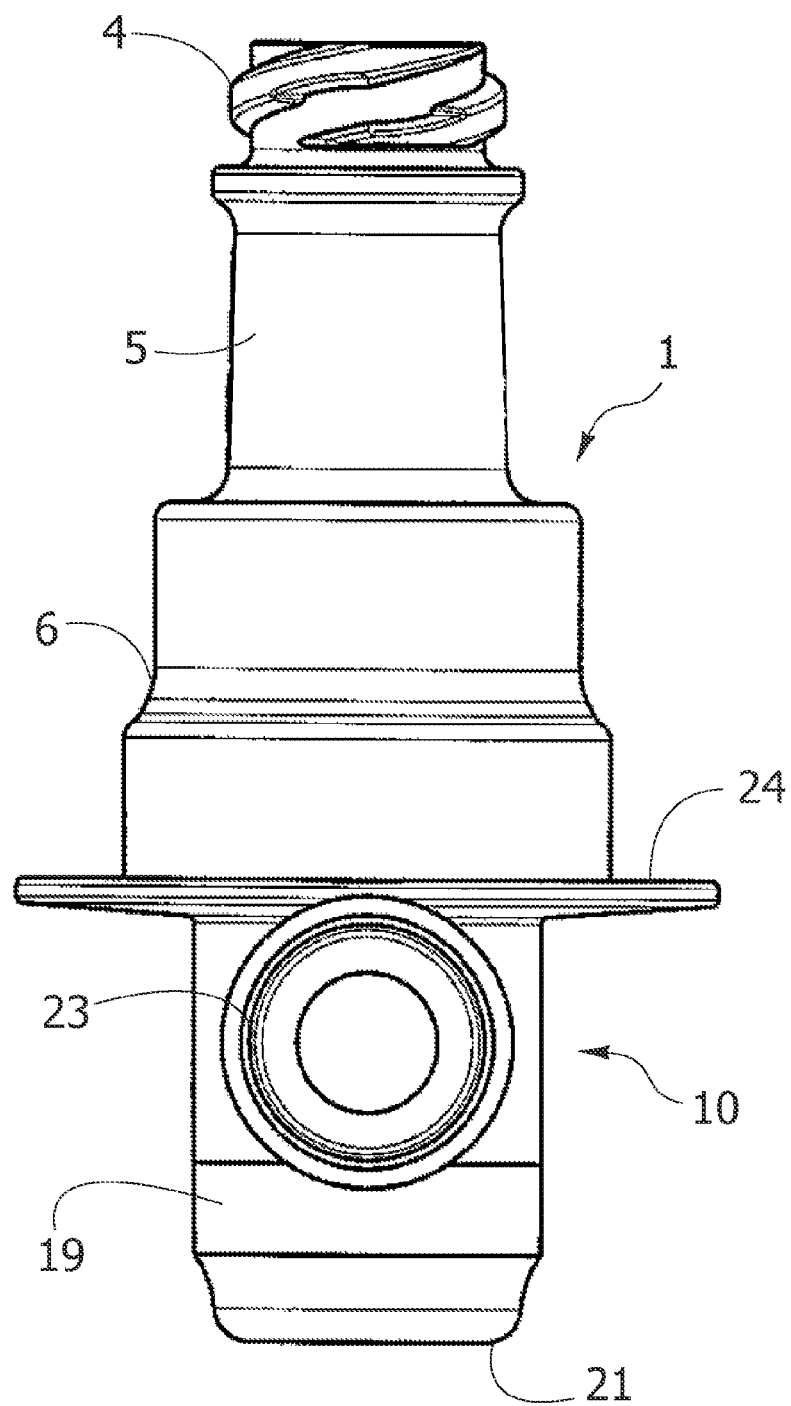
Figure 5:
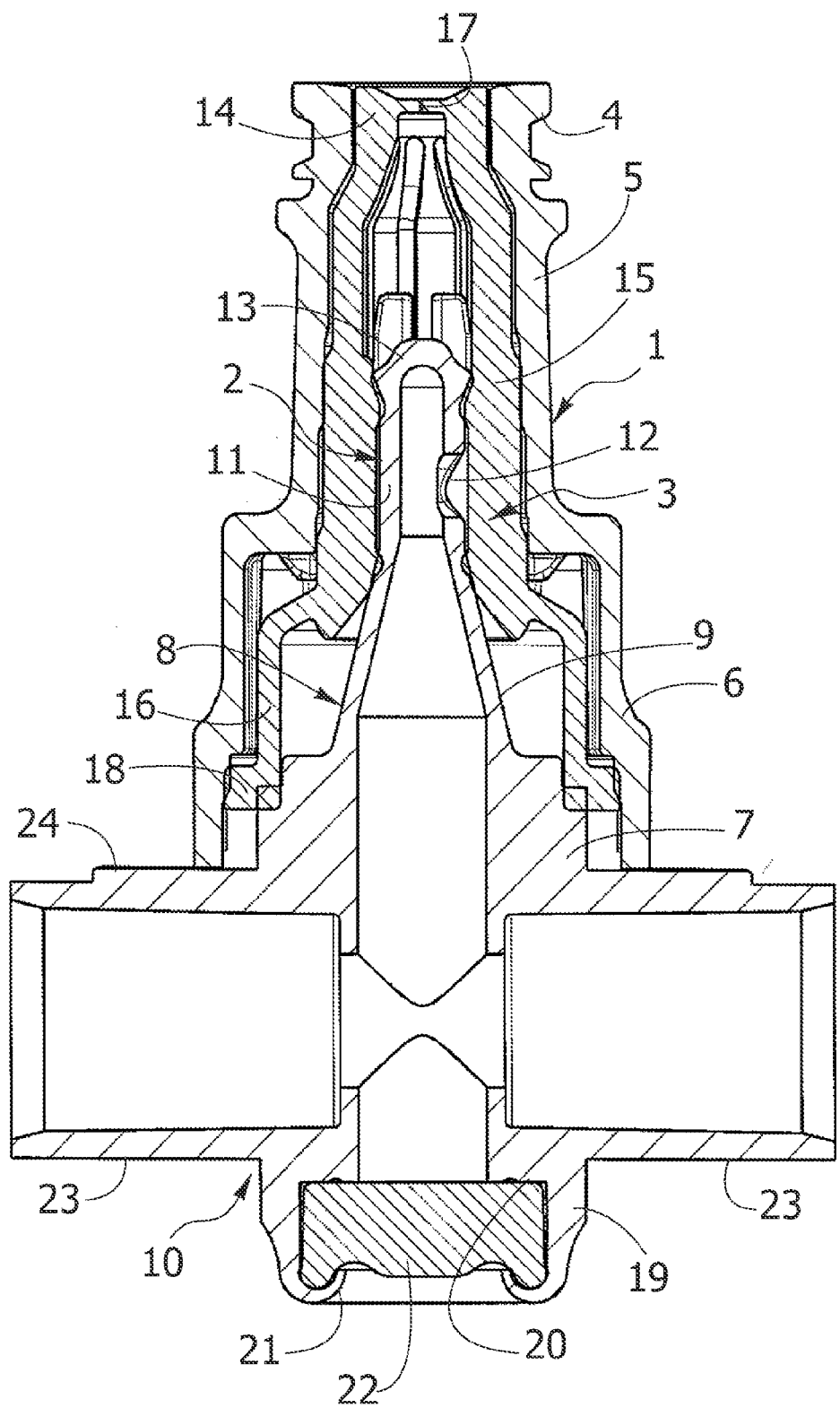
FIG. 5 is a view in axial cross and at a larger scale of the valve connector, represented in the deactivated condition.

With initial reference to FIGS. 1 to 5, the valve connector for medical infusion lines according to the invention is generally similar to the one described and illustrated in the aforesaid document No. EP-1834665A1 and basically includes three components: an external tubular body 1, an internal hollow spike 2 set axially within the cavity of the tubular body 1, and an elastic sealing member 3. Typically, the tubular body 1 and the hollow spike 2 are made of moulded rigid plastic material, whilst the sealing member 3 is made of an elastic material, for example, silicone rubber.

The tubular body 1 has an inlet end 4 formed like a female Luer-Lok connection member for engagement, in a generally conventional way, with a male Luer or Luer-Lok connection member of a fluid introducer, constituted, for example, by the tip of a needleless syringe.

The inlet end 4 is radiused to a generally cylindrical intermediate portion 5 of the tubular body 1, followed by a widened portion 6, which is also generally cylindrical.

The hollow spike 2 has a base part 7 that forms the outlet of the connector—which is designated as a whole by 10 and to which we shall return in what follows—, fixed to the edge of the widened terminal portion 6 of the tubular body 1. Branching integrally from the base 7 is a tubular pin 8 that includes an initial portion with a generally conical surface 9, followed by a generally cylindrical portion 11 formed with a lateral hole 12 and by a closed tip 13 facing the inlet 4 and located at a certain axial distance from this point.

The sealing member 3 comprises, in a single piece, an elastic head 14, a hollow elastic element 15, and an elastic base 16. The elastic head 14 has an outer surface generally complementary to the inner surface of the inlet 4 in such a way that it can be housed therein in a slidable way with a slight radial play, i.e., without interference. In the closed condition represented in FIG. 5, the head 14 is substantially undeformed and substantially flush with the edge of the inlet 4. Said head 14 is formed with an axial pre-slit or incision 17, which, in the undeformed closed condition of said head 14 within the inlet 4, is kept closed as a result of the elasticity of the head 14. In said condition, a protective anti-bacterial barrier is provided between the inside of the valve connector and the outside, ensuring at the same time the possibility of an effective cleaning conventionally performed using a swab soaked in disinfectant.

The elastic base 16 has, on the side opposite to the elastic head 14, a external annular flange 18 gripped and blocked axially between the widened portion 6 of the body 1 and the base part 7 of the hollow spike 2.

When a fluid introducer is inserted in the inlet 4 of the tubular body 1, the elastic head 14 is pushed axially towards the inside of the connector thanks to the elastic deformation of the sealing member 3, and the interaction between the elastic head 14 and the closed tip 13 of the hollow spike 2 produces opening of the pre-slit 17. The inlet 4 is thus set in communication, through the hole 12 and the cavity of the spike 11, with the outlet 10.

According to the peculiar aspect of the invention, the outlet 10 comprises a pierceable injection point set in condition coaxially facing the hollow spike 2. More in particular, the base part 7 of the hollow spike 2 has a terminal tubular appendage 19 formed with an internal annular shoulder 20 and with a turned-in external edge 21 set and blocked between which is an elastic diaphragm 22. Said diaphragm 22 defines, as has been said, a pierceable injection point, in the sense that it can be traversed, for example, by the needle of a syringe or else is provided with a pre-slit that can be opened as a result of the introduction, for example, of the cannula of a needle-less syringe.

In addition to the pierceable needle point thus defined, the outlet 10 of the valve connector according to the invention is moreover conveniently provided with at least one lateral tubular fitting set transverse to the tubular appendage of the terminal 19. In the case of the example illustrated, a pair of lateral tubular fittings is provided, set coaxially opposed to one another 23, for example, in the form of Luer cones, both formed integrally with the base part 7 of the hollow spike 2.

Figure 6:
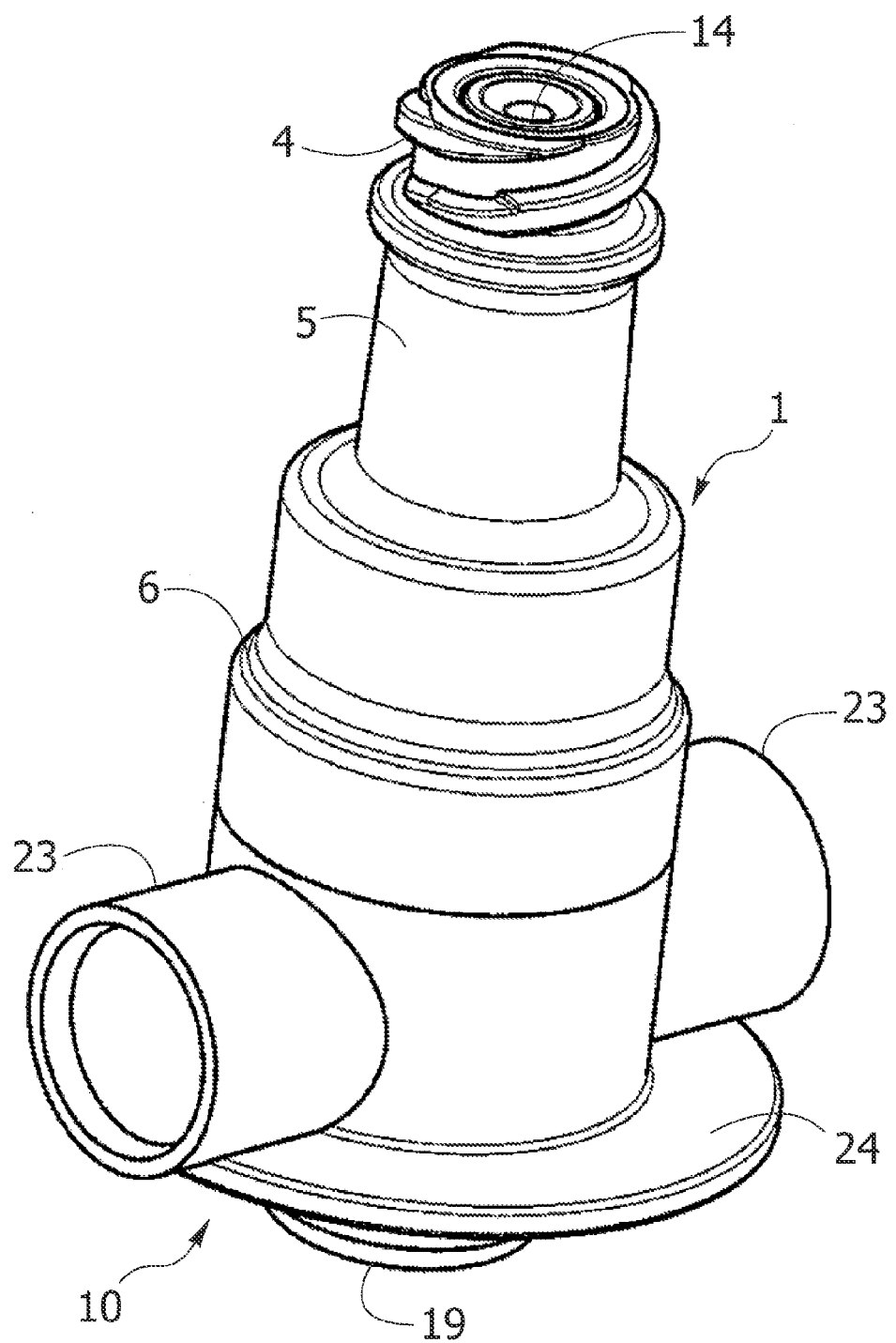
FIGS. 6 and 7 are views similar to those of FIGS. 1 and 2 that show a second embodiment of the valve connector according to the invention.
Figure 7:
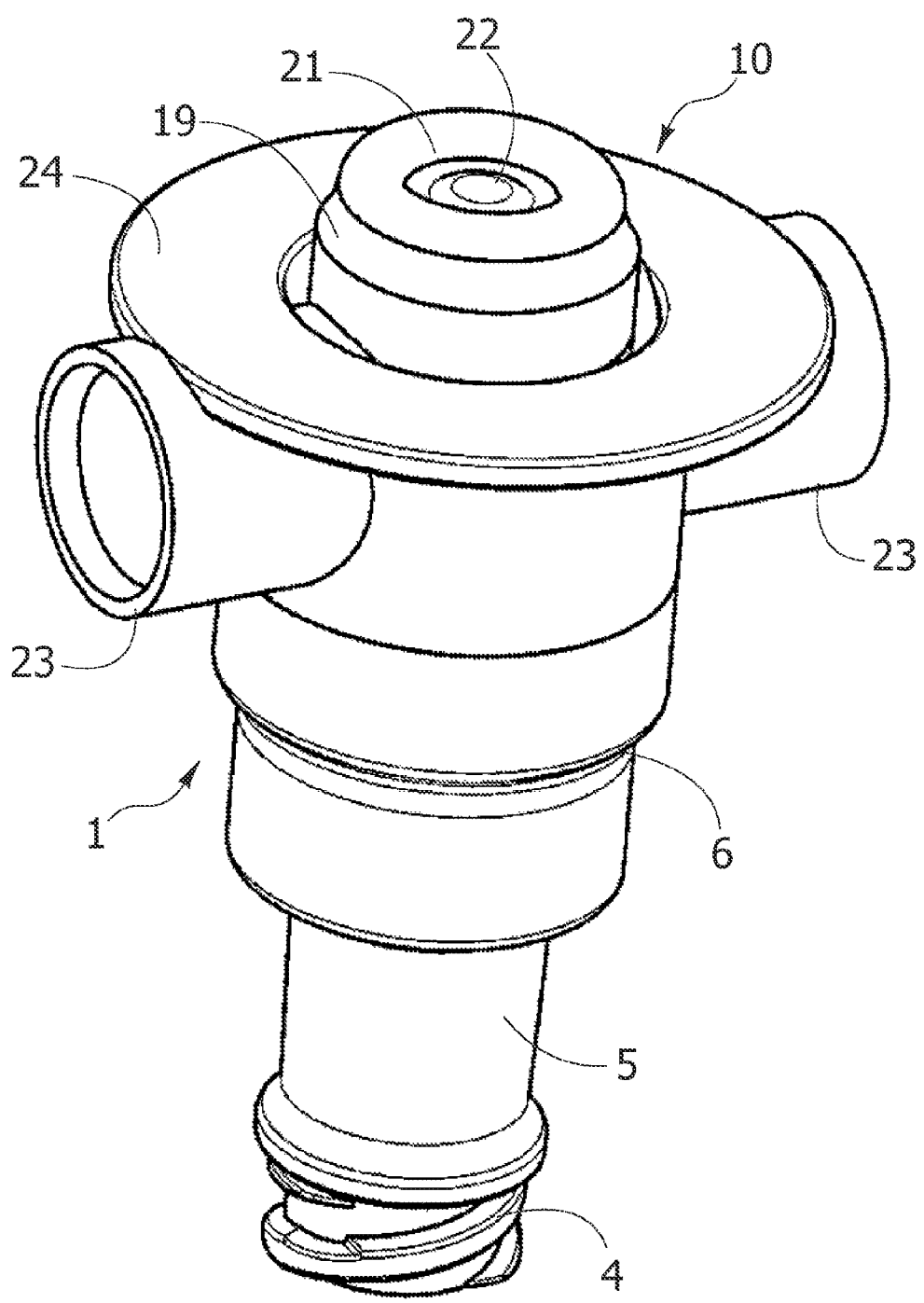
Figure 8:
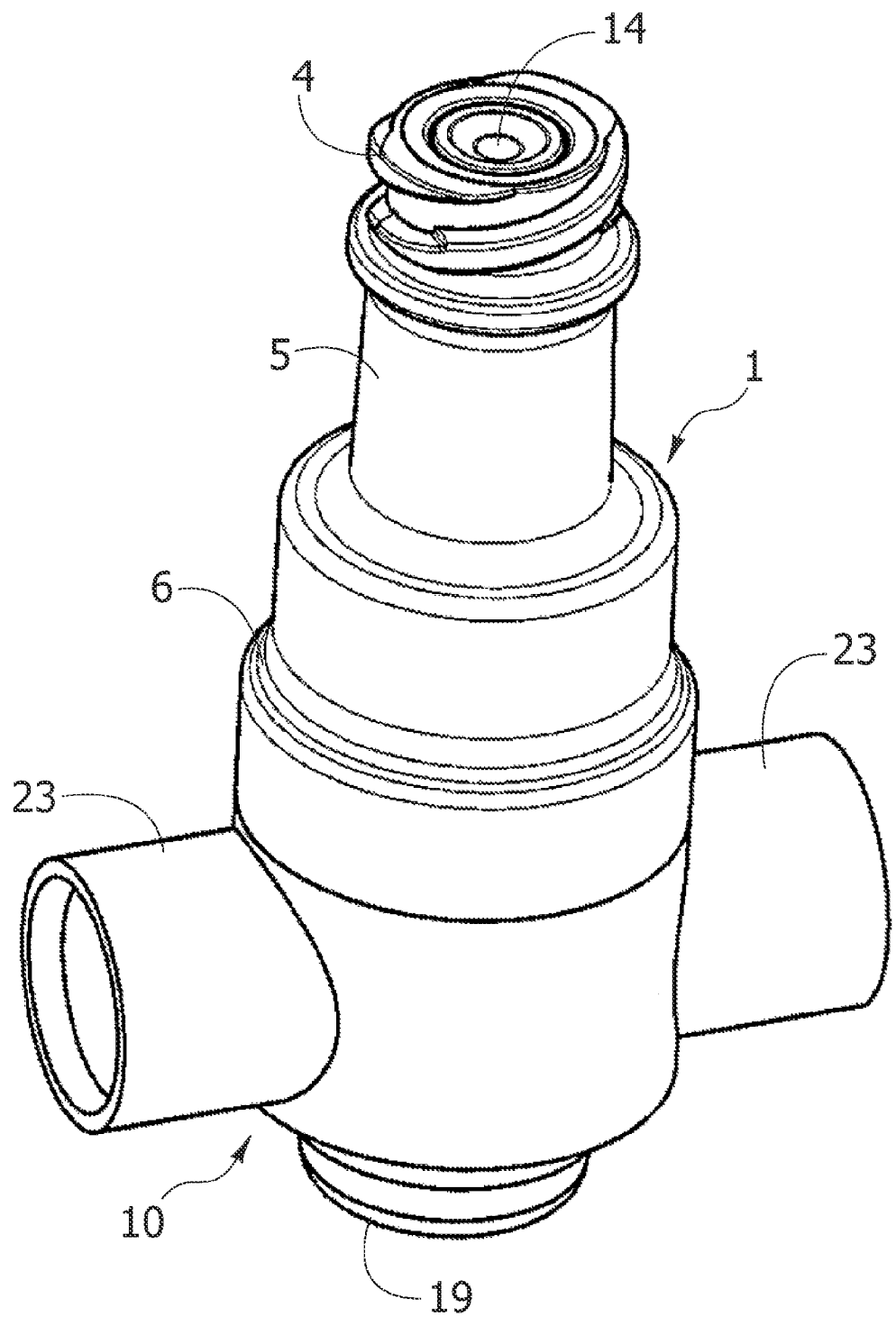
FIGS. 8 and 9 are two views, which are also similar to those of FIGS. 1 and 2 and show a third embodiment of the valve connector according to the invention.
Figure 9:
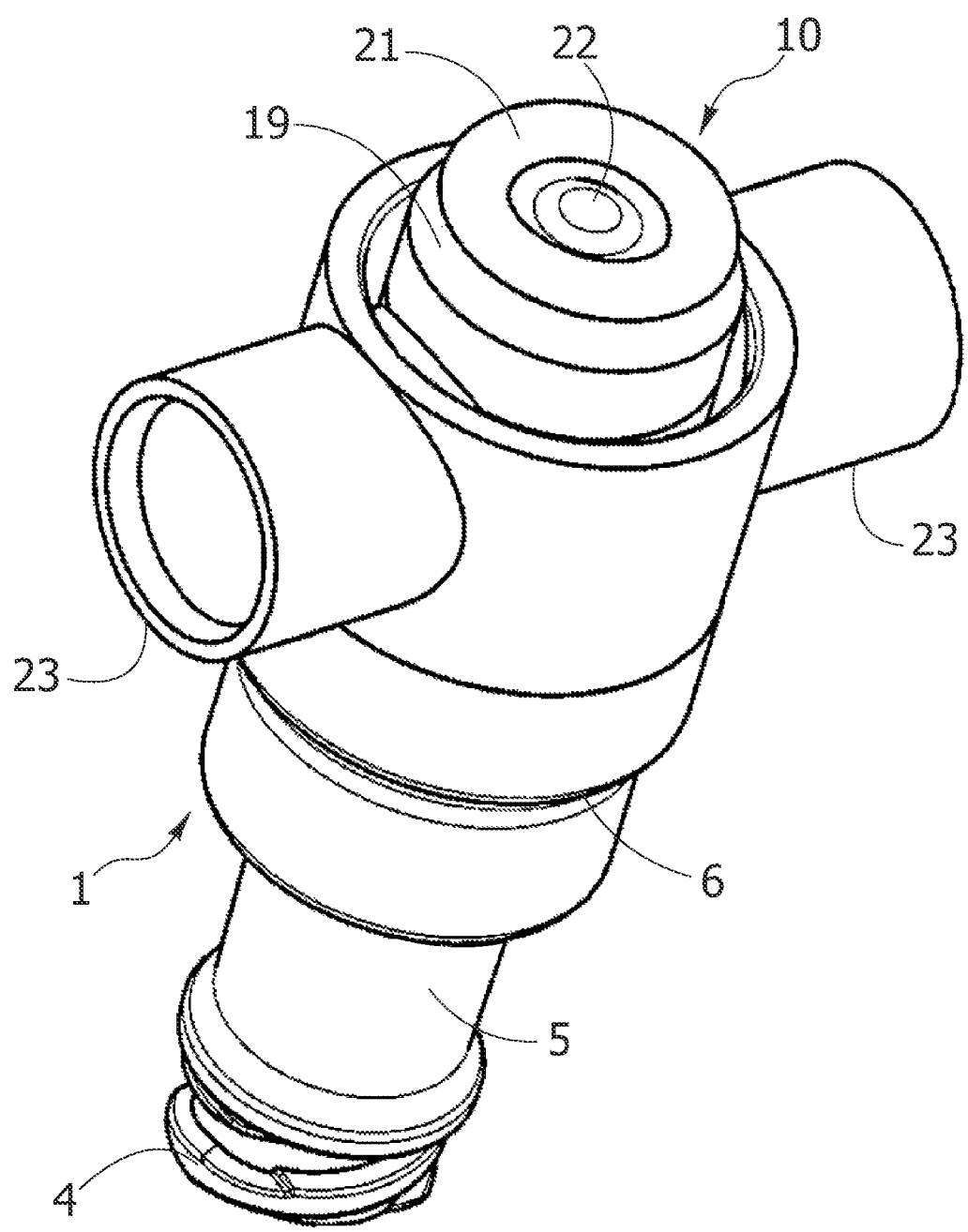

Designated by 24 is an external annular flange, which is also formed integrally with the base part 7 of the hollow spike 2. In the case of the embodiment described with reference to FIGS. 1 to 5, said flange 24 is situated between the lateral tubular fittings 23 and the widened part 6 of the body 1. In the case of the two variants of the invention illustrated in FIGS. 6, 7 and 8, 9 (where parts that are identical or similar to the ones described previously are designated by the same reference numbers), the annular flange 24 is, respectively, located between the lateral tubular fittings 23 and the terminal tubular appendage 19, or else, it is omitted.

Of course the details of construction and the embodiments may vary widely with respect to what has been described and illustrated herein, without thereby departing from the sphere of protection of the present invention, as defined in the ensuing claims.

What is claimed is:

1. A valve connector for medical infusion lines consisting of a tubular body having an inlet for insertion of a fluid introducer and an outlet, a hollow spike set axially within the cavity of the tubular body and having a closed tip facing said inlet and set at an axial distance from the latter, said hollow spike being in communication with said outlet of the tubular body, and a sealing member including an elastic head with a pre-slit, said elastic head being normally set in an undeformed condition within said inlet, in which said pre-slit is closed, and being displaceable axially against said closed tip of the hollow spike, as a result of insertion of said fluid introducer within the inlet, to assume an elastically deformed condition of opening of said pre-slit, said sealing member moreover including a hollow elastic element joined to said head and defining an elastic thrust means tending to keep said head in said undeformed condition, wherein said outlet comprises a pierceable injection point coaxially facing said hollow spike and consisting of a terminal tubular appendage formed integrally with said hollow spike, and a diaphragm made of elastic material blocked within said terminal tubular appendage, wherein said outlet further includes at least one lateral tubular fitting set transverse to said terminal tubular appendage, wherein the valve connector comprises a pair of lateral tubular fittings set coaxially opposed to one another, wherein said pair of lateral tubular fittings are formed integrally with said hollow spike and said terminal tubular appendage, wherein a flange is formed integrally with said pair of lateral tubular fittings, said hollow spike, and said terminal tubular appendage, and wherein said flange radially extends beyond an outer surface of the tubular body and over a substantial axial portion of each lateral tubular fitting, and wherein said terminal tubular appendage comprises an inner annular shoulder and an outer turned-in edge defining therebetween a blocking seat for said diaphragm made of elastic material.

* * * * *